United States Patent [19]
Brush et al.

[11] Patent Number: 5,808,044
[45] Date of Patent: *Sep. 15, 1998

[54] INDOCARBOCYANINE AND BENZINDOCARBOCYANINE PHOSPHORAMIDITES

[75] Inventors: Charles K. Brush, Whitefish Bay; Eric Dean Anderson, Oak Creek, both of Wis.

[73] Assignee: Pharmacia Biotech Inc., Milwaukee, Wis.

[*] Notice: The term of this patent shall not extend beyond the expiration date of Pat. No. 5,556,959.

[21] Appl. No.: 799,593

[22] Filed: Feb. 10, 1997

Related U.S. Application Data

[63] Continuation-in-part of Ser. No. 712,505, Sep. 11, 1996, abandoned, which is a continuation of Ser. No. 265,569, Jun. 24, 1994, Pat. No. 5,556,959, which is a continuation of Ser. No. 7,444, Jan. 22, 1993, abandoned.

[51] Int. Cl.$^6$ ............................. C07H 21/00; C12Q 1/68
[52] U.S. Cl. .................. 536/25.32; 536/25.3; 536/25.31; 536/241; 548/416; 548/455; 435/6
[58] Field of Search ................................. 536/25.32, 241, 536/25.3, 25.31; 548/416, 455; 435/6

[56] References Cited

U.S. PATENT DOCUMENTS

| | | |
|---|---|---|
| 4,981,977 | 1/1991 | Southwick et al. |
| 5,268,486 | 12/1993 | Waggoner et al. |
| 5,556,959 | 9/1996 | Brush et al. |
| 5,569,587 | 10/1996 | Waggoner. |
| 5,627,027 | 5/1997 | Waggoner. |

FOREIGN PATENT DOCUMENTS

| | | |
|---|---|---|
| WO 91/17169 | 11/1991 | WIPO. |
| WO 95/04747 | 2/1995 | WIPO. |

OTHER PUBLICATIONS

E. Anderson, et al., "Synthesis of a Carbocyanine Phsophoramidite and its use in Oligonucleotide Labeling," International Conference on Nucleic Acid Medical Applications, Jan. 15, 1993.

D. Andrews–Wilberforce and G. Patonay, "Fluorescene Quenching Studies of Near–Infrared Fluorophores," *App. Spectro.* 43(8):1450–1455, 1989.

Collaborative Research, Semiannual Progress Report No. 2, 1978.

B.H. Dahl, et al., "Mechanistic Studies on the Phosphoramidite Coupling Reaction in Oligonucleotide Synthesis. I. Evidence for Nucleophilic Catalysis by Tetrazole and Rate Variations with the Phosphorus Substituents," *Nucl. Acids Res.* 15(4):1729–1743, 1987.

J.H. Kenton, et al., "Improved Electrochemiluminescent Label for DNA Probe Assays: Rapid Quantitative Assays of HIV–1 Polymerase Chain Reaction Products," *Clin. Chem.* 38(6):873–879, 1992.

M. Mag and J.W. Engels, "Synthesis and Selective Cleavage of Oligodeoxyribonucleotides Containing Non–chiral Internucleotide Phosphoramidate Linkages," 17(15):5973–5988, 1989.

R.B. Mujumdar, et al., "Cyanine Dye Labeling Reagents Containing Isothiocyanate Groups," *Cytometry* 10:11–19, 1989.

(List continued on next page.)

*Primary Examiner*—James O. Wilson
*Attorney, Agent, or Firm*—Quarles & Brady

[57] ABSTRACT

A chemical compound of the following formula is disclosed:

where R is selected from the group consisting of H, trityl, 4-O-monomethoxytrityl, 4,4'-O-dimethoxytrityl, and acyl groups, and whereby R can be used as a protecting group or is an H;

R' is a phosphoramidite;

R" is selected from the group consisting of H and lower alkyl groups;

R'" is selected from the group consisting of H and lower alkyl groups;

R$^4$ is selected from the group consisting of H, lower alkyl, acyl, and $(CH_2)_p COO(CH_2)_q CH_3$ wherein p is an integer from 0 to 4 and q is an integer from 0 to 4;

R$^5$ is selected from the group consisting of H, lower alkyl, acyl, and $(CH_2)_p COO(CH_2)_q CH_3$ wherein p is an integer from 0 to 4 and q is an integer from 0 to 4;

n is an integer from 0 to 10;

m is an integer from 0 to 10;

r is 1, 2, or 3; and

X$^-$ is a negative ion.

9 Claims, 11 Drawing Sheets

OTHER PUBLICATIONS

Nippon Zeon, JP 62070391, 1987 (Abstract).

K.K. Ogilvie, et al., "Total Chemical Synthesis of a 77–nucleotide–long RNA Sequence having Methionine–acceptance Activity," *Proc. Natl. Acad. Sci. USA* 85:5764–5768, 1988.

G. Patonay and M.D. Antoine, "Near–infrared Fluorogenic Labels: New Approach to an Old Problem," *Analy. Chem.* 63(6):321–326, 1991.

J.C. Schulhof, et al., "The Final Deprotection Step in Oligonucleotide Synthesis is Reduced to a Mild and Rapid Ammonia Treatment by using Labile Base–protecting Groups," *Nucl. Acids. Res.* 15(2):397–416, 1987.

Sekine, et al., *J. Am. Chem. Soc.* 108:4581–4586, 1986.

H. Seliger and H.–H. Görtz, "Kenetik der Schutzgruppenabspaltung bei Derivaten des 2'–Desoxycytiden–5'–phosphats," *Chem. Ber.* 111:3732–3739, 1978.

P.L. Southwick, et al., "Cyanine Dye Labeling Reagents—Carboxymethylindocyanine Succinimidyl Esters," *Cytometry* 11:418–430, 1990.

H. Yu, et al., "Cyanine Dye dUTP Analogs for Enzymatic Labeling of DNA Probes," *Nucl. Acids Res.* 22(15):3226–3232, 1994.

H. Yu, et al., "Sensitive Detection of RNAs in Single Cells by Flow Cytometry," *Nucl. Acids Res.* 20(1):83–88, 1991.

Scheme 1

CCy = Indocarbocyanine

Scheme 2

Pam = P-(N(CH(CH$_3$)$_2$)$_2$)(CCH$_2$CH$_2$CN)

CCy = Indocarbocyanine

Pam = phosphoramidite
MMTr = monomethoxytrityl

XIVa

XIVb

MMTr = monomethoxytrityl

Pam = phosphoramidite

XIX

INDOCARBOCYANINE AND BENZINDOCARBOCYANINE PHOSPHORAMIDITES

This is a continuation-in-part of application Ser. No. 08/712,505 filed Sep. 11, 1996, now abandoned, which is a continuation of Ser. No. 08/265,569 filed Jun. 24, 1994, (now U.S. Pat. No. 5,556,959), which is a continuation of Ser. No. 08/007,444 filed Jan. 22, 1993, now abandoned.

FIELD OF THE INVENTION

In general, the present invention relates to indocarbocyanine dyes. Specifically, the present invention relates to the attachment of indocarbocyanine dyes to oligonucleotides.

BACKGROUND

Labelling of Oligonucleotides

Fluorescent, non-radioactive labelling is a highly desirable method for the detection of nucleic acids. For example, this method is useful in automated DNA sequencing, in situ detection of hybridization, detection of PCR products, structural studies, and any of several other applications. In the past, labelling of oligonucleotides has been most conveniently accomplished on an automated synthesizer by introduction of a derivatized deoxyuridine amidite[1] or a linker amidite bearing a protected primary amine[2,3] or thiol.[4] (By "oligonucleotide" we mean an oligomer of DNA, RNA, or modifications thereof, in the range of 3 to 200 bases in length.) Consequently, preparation of a labelled oligonucleotide requires synthesis of an oligonucleotide bearing the aforementioned modifications. The oligomer is deprotected, liberating the nucleophile, which can react with a fluorescent label. This procedure entails at least a partial purification of the deprotected oligomer, reaction with the fluorescent dye derivative, removal of the excess reagent, and purification of the labelled oligomer. The purification of the product is often tedious and addition of the label increases synthesis time considerably. The overall process requires approximately two days, compared to less than one day for preparation of the unlabelled oligonucleotide.

Current procedures for the preparation of other types of non-radioactively labelled oligonucleotides usually require similar procedures.[5] In general, after deprotection and purification, the liberated nucleophile is coupled with a label (fluorescent, bioreactive, chemiluminescent, photolabile, etc.).

A few examples of labelling amidites, which enable direct attachment to the oligonucleotide, have been reported. An amidite bearing a chemically inert bathophenanthroline-ruthenium complex has been prepared and proposed as a fluorescent label for DNA sequencing and as a diagnostic probe.[6] Biotin-containing amidites have been prepared by several groups,[7,8] and Teoule and co-workers have prepared amidites with dinitrophenyl, dansyl, and pyrenyl labels.[8] Du Pont workers have also reported the synthesis of succinylxanthene-labelled amidites.[9] Cech and co-workers have published the synthesis of a fluorescein amidite where the linker side-arm is attached to one of the phenolic hydroxyls.[10]

Indocarbocyanine Dyes

Indocarbocyanines have long been known for their dye properties.[11] Recently some indocarbocyanine derivatives have proved to be extremely fluorescent and are quite useful in the labelling of biomolecules.[12,13a-d] Because of the low background fluorescence of biological materials in the longer wavelength portion of the spectrum, the signal-to-noise ratio of analyses using these dyes is very good.

It is usually advantageous to use as little of labelled probe as possible in order not to perturb the biological system or process with the probe. Therefore, the better the signal-to-noise ratio, the less probe is necessary. Indocarbocyanines have a very high absorbance and are among the "brightest" of the common dyes used in biological labelling.[14]

Indocarbocyanines have been introduced into proteins via carboxamide[13b,14] and thiourea[15] linkages. One method[12] of linking an indocarbocyanine to a nucleic acid used the introduction of an amino linker to the 5'-end of the oligonucleotide. An N-hydroxysuccinimide (NHS) ester of the indocarbocyanine carboxylic acid was added to an amino-linked oligonucleotide and the resulting conjugate isolated and purified. An alternative procedure would involve the addition of a linker phosphoramidite to the 5' end of an oligonucleotide on a DNA synthesizer. After deprotection and desalting of the phosphoramidite-linked oligonucleotide, the active nucleophile then reacts with the indocarbocyanine-carboxylic acid NHS ester to yield labelled oligonucleotide. The groups present in the linker are preferred because they are stable to conditions used in DNA synthesis, sequencing, and hybridization studies, as well as stability in long-term storage.

In spite of the long time for reaction and workup (compared to the synthesis of the oligonucleotide), generally introduction of labels has been done after deprotection of the oligonucleotide. Reaction and workup normally requires two days.

For these reasons, there is a need in the art of oligonucleotide labelling for an indocarbocyanine-linked phosphoramidite which allows the labelling of oligonucleotides in one step.

Indocarbocyanines have been conjugated to phosphitylating moieties for the purpose of labeling oligonucleotides on an automated DNA synthesizer. Benzindocarbocyanines have similar properties but wavelengths slightly longer than indocarbocyanines. Benzindocarbocyanines are more aromatic and hydrophobic in character. Consequently they would not normally be expected to be useful for labeling of biological molecules, without solubilizing groups. It is beneficial to be able to make small changes in wavelength to optimize the fit of the dye absorption and emission spectra to available lasers and detectors. In the present invention, synthesis of phosphoramidites and labeled oligonucleotides is disclosed.

SUMMARY OF THE INVENTION

One aspect of the present invention is directed to chemical compound of the following formula:

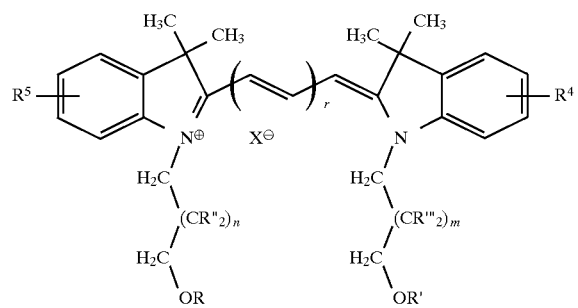

wherein:

R is selected from the group consisting of H, trityl, 4-O-monomethoxytrityl, 4,4'-O-dimethoxytrityl, and acyl groups,

and whereby R can be used as a protecting group or is an H;
R' is a phosphoramidite;
R" is selected from the group consisting of H and lower alkyl groups;
R'" is selected from the group consisting of H and lower alkyl groups;
$R^4$ is selected from the group consisting of H, lower alkyl, acyl,

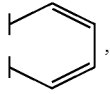

and $(CH_2)_pCOO(CH_2)_qCH_3$ wherein p is an integer from 0 to 4 and q is an integer from 0 to 4;
$R^5$ is selected from the group consisting of H, lower alkyl, acyl,

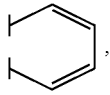

and $(CH_2)_pCOO(CH_2)_qCH_3$ wherein p is an integer from 0 to 4 and q is an integer from 0 to 4;
n is an integer from 0 to 10;
m is an integer from 0 to 10;
r is 1, 2, or 3; and
$X^-$ is a negative ion.

A preferred version of the chemical compound is where R is 4-O-monomethoxytrityl; R' is N,N-diisopropyl-O-β-cyanoethyl phosphoramidite; R" and R'" are H; n is 1; m is 1; r is 2; and $R^4$ and $R^5$ are 5,6-butadienyl.

Another preferred version of the chemical compound is where R is 4-O-monomethoxytrityl; R' is N,N-diisopropyl-O-β-cyanoethyl phosphoramidite; R" and R'" are H; n is 1; m is 1; r is 1; and $R^4$ and $R^5$ are 5,6-butadienyl.

A still further preferred version of the chemical compound is where R is acetyl; R' is N,N-diisopropyl-O-β-cyanoethyl phosphoramidite; R" and R'" are H; n is 1; m is 1; r is 2; and $R^4$ and $R^5$ are 5,6-butadienyl.

Another aspect of the invention provides a chemical compound of the following formula:

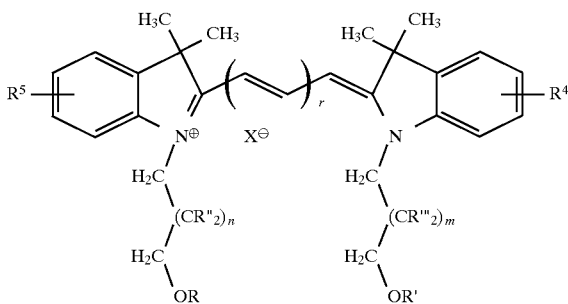

wherein:
R is selected from the group consisting of aryl-group-containing moieties, wherein the moiety does not interfere with the attachment of an oligonucleotide at the R' position;

R' is a oligonucleotide;
R" is selected from the group consisting of H and lower alkyl groups;
R'" is selected from the group consisting of H and lower alkyl groups;
$R^4$ is selected from the group consisting of H, lower alkyl, acyl,

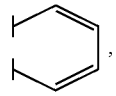

and $(CH_2)_pCOO(CH_2)_qCH_3$ wherein p is an integer from 0 to 4 and q is an integer from 0 to 4;
$R^5$ is selected from the group consisting of H, lower alkyl, acyl,

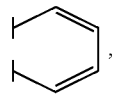

and $(CH_2)_pCOO(CH_2)_qCH_3$ wherein p is an integer from 0 to 4 and q is an integer from 0 to 4;
n is an integer from 0 to 10;
m is an integer from 0 to 10;
r is 1, 2, or 3; and
$X^-$ is a negative ion.

A further aspect of the present invention is a benzindocarbocyanine dye attached to a phosphoramidite. The dye comprises a benzindolinium ring and a benzindolenine ring in resonance wherein said rings are connected by a carbon chain with conjugated double bonds, wherein the rings each have a dimethyl substituent at the 3 position, wherein said phosphoramidite is attached through a first linker at the nitrogen of either ring, wherein a protecting group is attached through a second linker at the nitrogen of the other ring, and wherein no glyceryl linker is interposed between (a) said protecting group and said phosphoramidite and (b) said benzindocarbocyanine dye.

Another aspect of the present invention is a indocarbocyanine dye attached to a phosphoramidite. The dye comprises an indolinium ring and an indolenine ring in resonance connected by a carbon chain with conjugated double bonds. Each ring has a dimethyl substituent at the 3 position. The attachment of the dye to the amidite is through a linker at the nitrogen of either ring.

Another aspect of the present invention is directed to a method of attaching a fluorescent label to an oligonucleotide wherein the above compound serves as the fluorescent label.

Another aspect of the invention involves attaching a fluorescent label to an oligonucleotide by reacting the above compounds to the oligonucleotide such that the label becomes linked to the oligonucleotide at any point in the oligonucleotide chain. A preferred version of this aspect of the invention comprises linking a 5' end of the oligonucleotide to a phosphorus on the compound, oxidizing the linkage product, and removing the protecting group R from the oxidized linkage product. A preferred version of this inventive aspect comprises the presence of tetrazole and acetonitrile during the linkage reaction.

It is an object of the present invention to provide an indocarbocyanine and a benzindocarbocyanine dye in an amidite form.

It is another object of the present invention to provide a direct method of attaching an indocarbocyanine and a benzindocarbocyanine dye to an oligonucleotide.

It is an advantage of the present invention that an indocarbocyanine and a benzindocarbocyanine dye may be attached to an oligonucleotide in a one-step procedure.

These and other features, aspects, and advantages of the present invention will become better understood with regard to the following description, appended claims, and accompanying drawings.

When we refer to "lower alkyl" we mean those alkyl groups having 1–6 carbons. When we refer to "acyl" we mean the group RCO— where R is a lower alkyl or acyl group.

Description of the Invention

Figure 1:
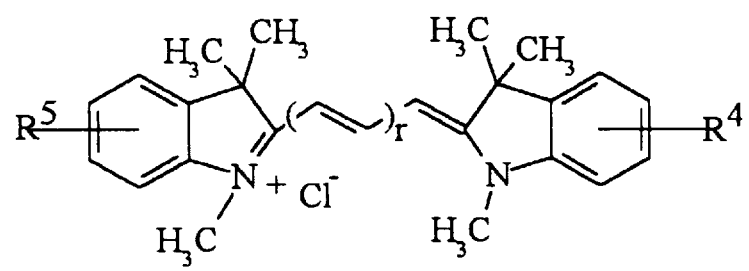
FIG. 1 shows the general structure of indocarbocyanine known in the prior art.

Indocarbocyanines have long been known for their dye properties.[11] Recently some indocarbocyanine derivatives have proved to be extremely fluorescent and are quite useful in the labelling of biomolecules.[12,13a-d] Indocarbocyanines of the general structure I (r=2) (in FIG. 1) fluoresce in the red region of the visible spectrum ($\lambda_{max}$ absorbance≅650 nm; $\lambda_{max}$ emission≅670 nm).[13b] When r=1, $\lambda_{max}$ absorbance≅552 nm; $\lambda_{max}$ emission≅570 nm.[13b] Because of the low background fluorescence of biological materials in the longer wavelength portion of the spectrum, the signal-to-noise ratio of analyses using these dyes is very good. It is advantageous to use as little as possible of labelled probes in order not to perturb the biological system or process with the probe. Therefore, the better the signal-to-noise ratio, the less probe is necessary. Indocarbocyanines have a very high absorbance ($\epsilon_{max}$≅215,000 for I (r=2), $\epsilon_{max}$≅130,000 for I (r=1)), an excellent fluorescent yield, and are among the "brightest" of the common dyes used in biological labelling.[14]

Figure 2:
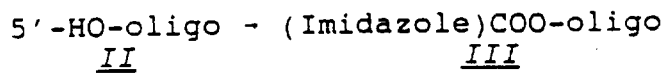
FIG. 2 shows prior art schemes for linking an indocarbocyanine to a nucleic acid.
Figure 2:
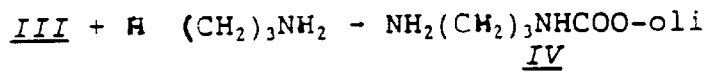
Figure 2:
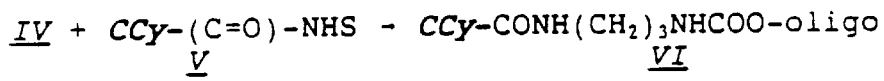
Figure 2:
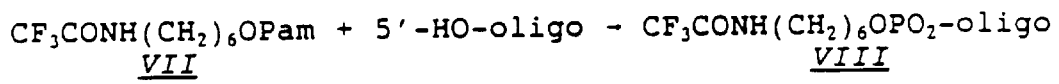
Figure 2:
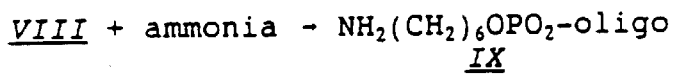
Figure 2:
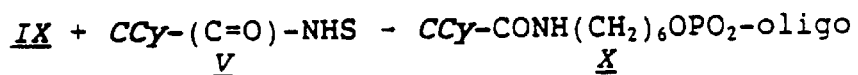

One prior art method[12] of linking an indocarbocyanine to a nucleic acid used the introduction of an amino linker to the 5'-end of the oligonucleotide, as shown in Scheme 1 (in FIG. 2). An N-hydroxysuccinimide (NHS) ester of the indocarbocyanine carboxylic acid V was added to amino-linked oligo IV and the resulting conjugate VI isolated and purified.

An alternative prior art procedure (as shown in Scheme 2 in FIG. 2) could be the addition of a linker phosphoramidite, such as VII, to the 5'-end of an oligonucleotide on a DNA synthesizer. After deprotection and desalting of VIII, the active nucleophile in IX reacts with the indocarbocyanine-carboxylic acid NHS ester V to yield labelled oligonucleotide X. The groups present in the linker are preferred because they are stable to conditions used in DNA synthesis, sequencing, and hybridization studies, as well as stability in long-term storage. In spite of the long time for reaction and workup (compared to the synthesis of the oligonucleotide), introduction of indocarbocyanines has been done after deprotection of the oligonucleotide.

Figure 7:
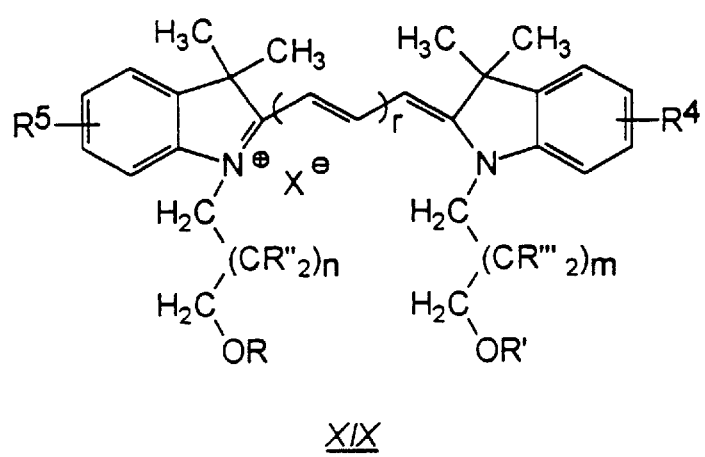
FIG. 7 shows the indocarbocyanine phosphoramidite of the present invention.

In order to facilitate the introduction of indocarbocyanine dye labels to oligonucleotides, we have synthesized novel phosphoramidites of several indocarbocyanine dyes, as shown by structure XIX in FIG. 7. The indocarbocyanine-linked phosphoramidite can be used directly on any DNA synthesizer to automatically add the dye to any nucleotide position, including the preferred 5'-end of the oligomer. The time for the coupling step (two minutes) and the concentration of reagent needed (0.1M) is the same as for the usual nucleoside phosphoramidites.[16] By the use of nucleoside protecting groups that are rapidly removed,[17] the total time for the preparation of a 20 base long labelled oligonucleotide is reduced from two days, as described above, to five hours. The yield of labelled product is also greater and the purification simpler than in the two-step method.

Consideration of the chemistry of oligonucleotides and indocarbocyanines was observed in the design of the invention. Since indocarbocyanines are generally unstable to basic conditions,[11] mild conditions for the rapid removal of protecting groups are necessary to deprotect an oligonucleotide bearing an indocarbocyanine moiety. Some nucleoside protecting groups can be removed under relatively mild conditions, especially the commercially available phenoxyacetyl protection,[17] making possible the improved method of attaching indocarbocyanines to oligonucleotides. The inclusion of an acid labile trityl group in the molecule allows the dye to be inserted anywhere in the oligonucleotide, or to have additional modifying groups present, such as a hydrophilic phosphate or a second dye moiety.

Figure 3:
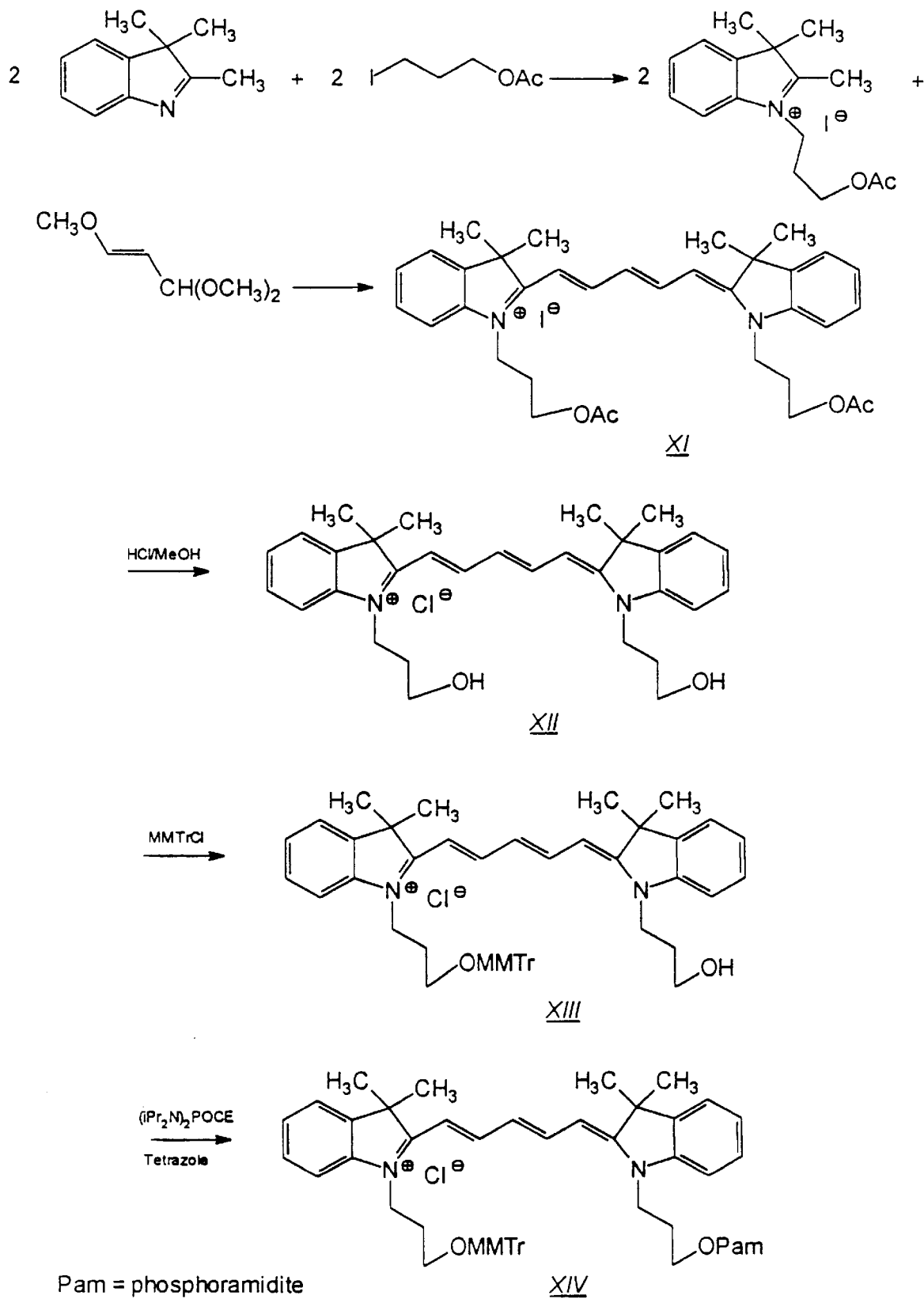
FIG. 3 shows a reaction scheme for the preparation of one version of the indocarbocyanine phosphoramidite of the present invention.

The general synthetic scheme for the preparation of a typical preferred indocarbocyanine phosphoramidite is shown in FIG. 3. The synthesis of the intermediate indocarbocyanine XI follows a modification of a standard literature method.[13b] If $R_4$ and $R_5$ are H, starting materials are readily commercially available. If $R_4$ or $R_5$ are not H, the starting materials are not commercially available. Methods to produce these compounds are generally known to those of skill in the art. For example, Smithwick[13b] describes the preparation of modified indolenines. Suitable specific procedures are detailed below in the Examples.

Compounds XI and XII are symmetrical in their structures, since the double bond system resonates between the two nitrogens, leading to an averaging of the electron density throughout the chromophore. The preparation of a pure intermediate therefore is simpler for the preferred compound than if it were composed of dissimilar indolenines, which can result in cross-coupling and a mixture of products. However, the invention can be prepared with dissimilar indolenines if desired.

Figure 4:
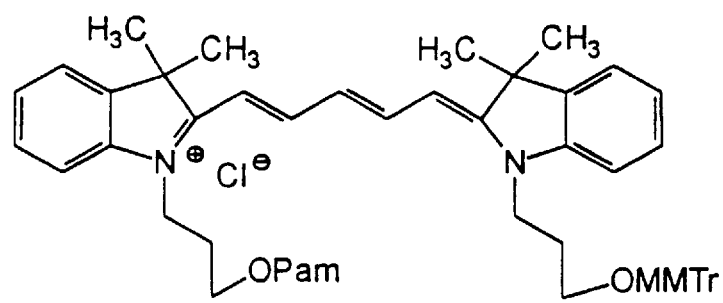
FIG. 4 shows the equivalence of tritylation in the version of indocarbocyanine phosphoramidite depicted in FIG. 3.
Figure 4:
Figure 4:
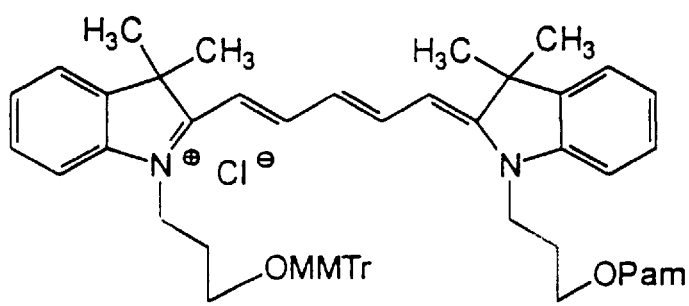

One novelty of the synthesis lies in the protection of one of the hydroxyls of compound XII, so that the other can be converted to the phosphoramidite (XIV). Since XII is symmetrical, it does not matter on which side the tritylation or acylation occurs. The ultimate phosphoramidites are identical, as shown in FIG. 4.

Neither the trityl nor phosphoramidite function has been introduced into indocarbocyanines previously. The amidite XIV has a visible spectrum characteristic of indocarbocyanines ($\lambda_{max}$ absorbance at 644 nm in dichloromethane)[13b] Labelled oligonucleotides prepared from XIV have $\lambda_{max}$ absorbance at 648 nm, the same $\lambda_{max}$ as labelled oligonucleotides prepared from the two step procedure outlined in Scheme 1, FIG. 2.[12]

Use of the various trityl groups, all of which are removable under acidic conditions, adds versatility to the invention. The monomethoxytrityl is preferred for its balance of stability during synthesis and ease of removal when desired. However, other protecting groups, such as dimethoxytrityl or acyl groups, are suitable for the present invention.

Figure 5:
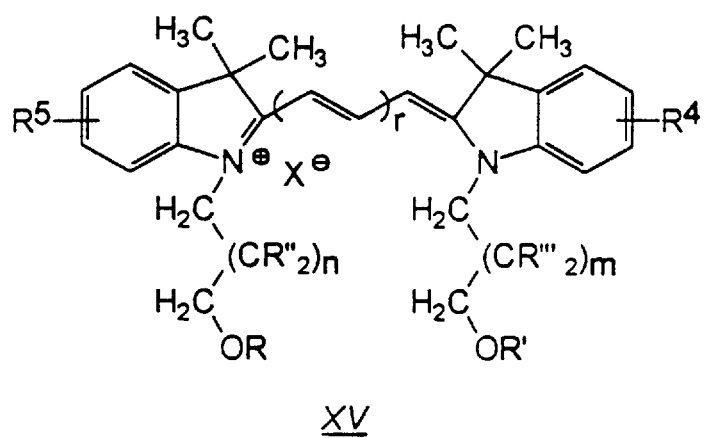
FIG. 5 shows a version of the indocarbocyanine phosphoramidite of the present invention after the reactions to add it to an oligonucleotide.

The dimethoxytrityl group is routinely removed by mild acid treatment in the cycle for synthesis of oligonucleotides with nucleoside phosphoramidites.[16] The indocarbocyanine moiety derived from the amidite can be treated as a nucleotide, in that it can be added anywhere in the sequence (R=oligonucleotide-5'-OH, R'=oligonucleotide-3'-OH, FIG. 5, XV), including the 3'-end (FIG. 5, XV, R=H, R'=oligonucleotide-3'-OH).

The preferred point of addition is the 5'-end of the oligonucleotide, where interference with hybridization by the dye label is minimized. Removal of the trityl group leaves a hydroxyl group (XVI, FIG. 6), which is the commonly used form. If it is desired to make the dye portion of the molecule more hydrophilic, a commercially available phosphorylating amidite can be used to introduce a phosphate group after detritylation of the (XVII, FIG. 6). At this point, a variety of aryl group-containing moieties may be added to the dye. By "aryl-group containing moieties" we mean groups that are capable of being added to the compound of the present invention at the R position after oligonucleotide coupling and should not interfere with the oligonucleotide. This moiety may have an advantageous effect on the fluorescence of the indocarbocyanine dye. An example, described in FIG. 6, is the addition of a second indocarbocyanine dye.

Figure 6:
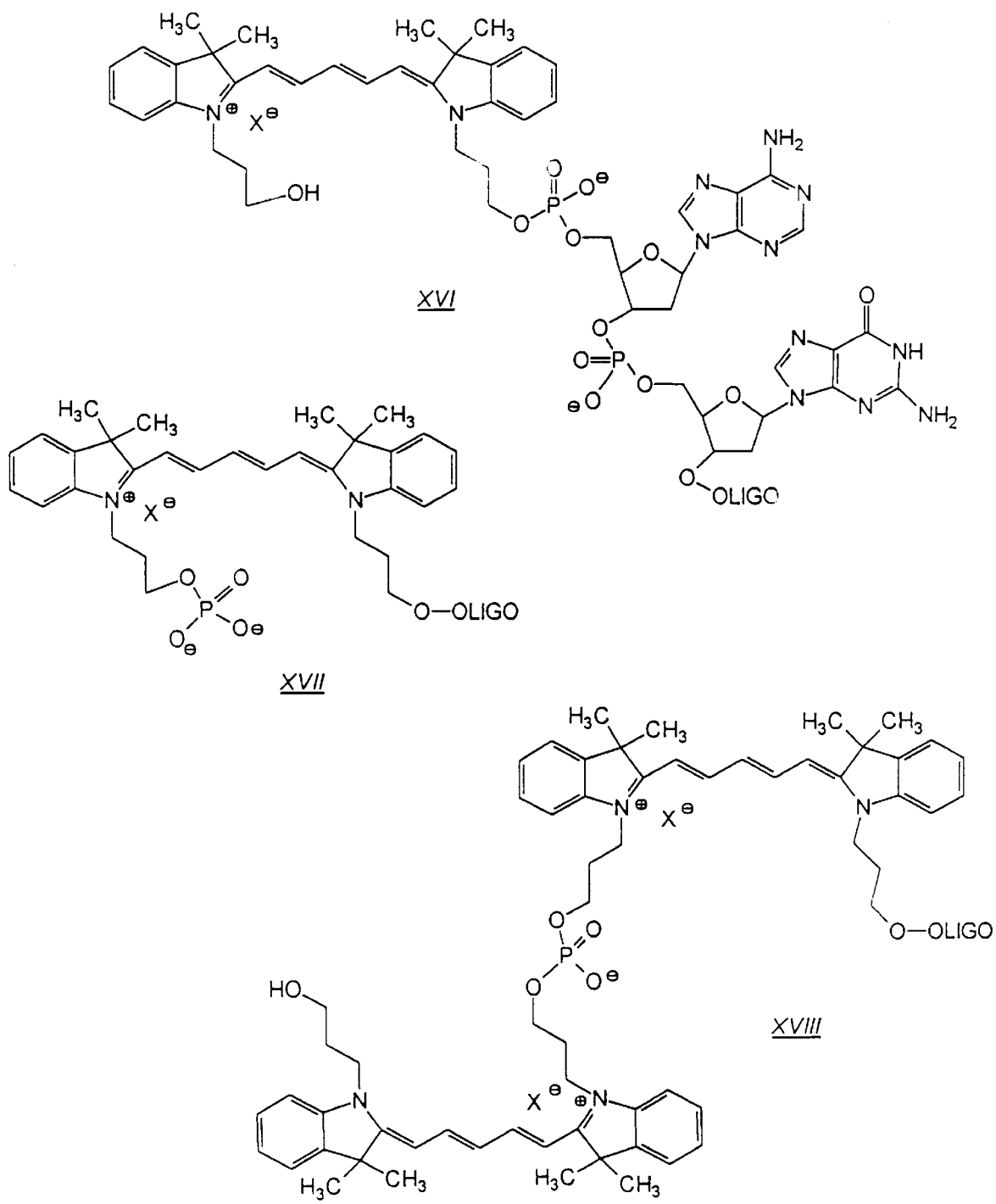
FIG. 6 shows various versions of the indocarbocyanine phosphoramidite of the present invention after linkage to oligonucleotides.

Addition of a second indocarbocyanine is possible by a second coupling of the dye-amidite (XVIII, FIG. 6). Also, other dyes which are available as amidites may be added in the same way to give a multi-color labelled oligonucleotide. Specific examples of suitable dyes are XIX where r=1 or 3 and R''-R$^5$=H and n=m=1; fluorescein; rhodamine; and acridine. Such multi-colored labelled oligonucleotides may be useful in multiple excitation and/or multiple detection mode instruments, or in detection by fluorescence resonance energy transfer.[18]

The synthesis of indocarbocyanine phosphoramidite XIX (FIG. 7), in which r=1, n=m=1, R=MMTr, and R'=β-cyanoethyl-N,N-diisopropyl phosphoramidite, is accomplished by a single modification: the use of a one carbon unit instead of a three carbon unit in the condensation step.[13b] It is as versatile as XIV in its chemistry, but has a $\lambda_{max}$ absorbance at 552 nm and $\lambda_{max}$ emission at 570 nm. We envision that r may be either 1, 2, or 3.

One significance of this invention lies in the fact that indocarbocyanines, a useful label for fluorescent detection in biomolecules and of significance in DNA sequencing, can now be added to an oligonucleotide in a single automated step on any DNA synthesizer. The overall preparation and purification time to prepare dye-linked oligonucleotides is decreased from two days to 5 hours. Use of the indocarbocyanine amidite obviates the reaction of oligonucleotide and label after completion of the synthesis and deprotection. Furthermore it is not necessary to separate the product from a large excess of labelling reagent. Due to the lability of the indocarbocyanine moiety in concentrated ammonia at 55° C. for 5–16 hours, the use of phenoxyacetyl protection for the heterocyclic bases is recommended.

The compound of the present invention, as disclosed in compound XIX, possesses an X$^-$ moiety. X$^-$ indicates the presence of a negative ion. Preferably, this ion is a halide. Most preferably, it is a chloride ion.

EXAMPLES

All numbers in the following examples refer to the general structure XIX in FIG. 7, except as otherwise noted.

Example 1

(XIX, r=2, n=m=1, R=MMTr, R'=N,N-diisopropyl-O-β-cyanoethyl phosphoramidite, R''=R'''=R$^4$=R$^5$=H, same as XIV).

1-(3''-(1''-(β-Cyanoethyl-N,N-diisopropylphosphoramidite)-propyl))-1'-(3'''-(1'''-(p-methoxytrityl)oxypropyl))-3,3,3',3'-tetramethyl-indodicarbocyanine chloride.

3-Iodo-1-propyl acetate

3-Chloro-1-propyl acetate (45 mL, 50 g, 0.3661 mol, Aldrich) was added with stirring to 300 mL of anydrous acetone, followed by 109.74 g (0.7322 mol., Baker) of NaI. The reaction was heated to reflux for a minimum of 17 hours. The acetone was evaporated and 300 mL of ether was added. The mixture was stirred, filtered, and the salts were washed with 200 mL of ether. The filtrate was extracted three times with water, dried with sodium sulfate, and the solvent evaporated. The residual oil was dried under vacuum overnight. Yield: 80–90% of 3-iodo-1-propyl acetate.

1-((3'-(1'-Acetoxypropyl))-2,3,3-trimethyl-(3H)-indolinium iodide

3-Iodo-1-propyl acetate (42 mL, 0.315 mol) was heated in a round bottom flask in an oil bath to 50° C. 2,3,3-Trimethyl-(3H)-indole (0.315 mol, 50.2 g, 52.3 mL, Kodak) was added and the temperature raised to 100° C. The mixture was heated at 100° C. for two to three hours, then cooled to room temperature. The gummy solid was dissolved in 250 mL 10% methanol/dichloromethane and 600 mL of ether was added. Crystallization took place overnight; the crystals were collected, washed with more ether, and dried in vacuo. Yield: 85–95% of 1-(1'-acetoxypropyl)-2,3,3-trimethyl-(3H)-indolinium iodide.

1,1'-Bis-(3''-(1''-hydroxypropyl))-3,3,3',3'-tetramethyl-indodicarbocyanine chloride (XIII 1-(1'-Acetoxypropyl)-2,3,3-trimethyl-(3H)-indolinium iodide (110 g, 0.284 mol) was dissolved in 800 mL dry acetonitrile with 24 mL (0.177 mol) of TEA and 8 mL (0.136 mol) of acetic acid in a round bottom flask in an oil bath heated to 100° C. In a dropping funnel, 1,3,3-trimethoxypropene (28.15 g. 0.45 mol, Kodak) was dissolved in 123 mL of dry acetonitrile. The mixture was added dropwise to the reaction flask over a period of one hour. The reaction was refluxed for 2 hours after the addition of the trimethoxypropene, during which time the progress was monitored by TLC and spectrophotometer readings. The starting material peak at 280 nm diminished as the product peak at 640 nm increased. When there was no change in the ratio of peak heights, the reaction mixture was cooled and evaporated to a gum.

The residue was dissolved in 3.2 L of 2M HCl in 50:50 water/methanol and stirred overnight at room temperature.

The solvent was evaporated and the residue partitioned between dichloromethane and water. The organic layer was dried with sodium sulfate and the solvent evaporated. The residue was purified by column chromatography on silica gel using a mixture of 5/5/5/85 methanol:acetone:ethyl acetate:dichloromethane, followed by 8/8/8/76 of the same components. The appropriate fractions were pooled and evaporated to yield 60 g of 1,1'-bis-(3"-(1"-hydroxypropyl))-3,3,3',3'-tetramethyl-indodicarbocyanine chloride (XII). Purity of the product was monitored using HPLC (80% acetonitrile/20% 0.1M TEAA mobile phase, C18 column 4.6×250 mm, flow rate: 1 mL/min, detector: 640 nm).

$^1$H NMR (CDCl$_3$): δ, 7.92, t, 2H, β-CH=; 7.4–7.17, m, 8H, aromatic; 7.01, t, 1H, λ-CH=; 6.51, d, 2H, α-CH=; 4.26, br t, 4H, 3'-CH$_2$; 3.85, br t, 4H, 1'-CH$_2$; 2.10, br m, 4H, 2'-CH$_2$; 1.70, s, 12H, CH$_3$. UV/visible spectrum: λ$_{max}$ 642 (598, sh.) nm; 324, 282, 248 nm.

1-(3'"-(1'"Hydroxypropyl))-1'-(3"-(1"-(p-methoxytrityl)oxypropyl))-3,3,3',3'-tetramethyl-indodicarbocyanine chloride (XIII)

Compound XII (6 g, 0.012 mol) was dried by co-evaporation three times with acetonitrile. It was dissolved in 65 mL of dry pyridine and 3.29 g (0.0108 mol) of monomethoxytrityl chloride (Aldrich) was added. The reaction was monitored by TLC and small increments of monomethoxytrityl chloride were added until the appearance of the bis-trityl compound began. The reaction was quenched by the addition of methanol and the mixture evaporated to dryness. The residue was purified on a silica gel column with 3/3/3/91 methanol:acetone:ethyl acetate:dichloromethane, followed by 5/5/5/85 as the eluent. The unreacted dihydroxy compound was recovered by stripping the column with 50/50 methanol:dichloromethane. Yield of compound XIII was 3–4 g. Purity was determined by HPLC (90% acetonitrile/10% 0.1M TEAA mobile phase, C3 column 4×60 mm, flow rate: 1 mL/min, detector: 640 nm). The purified compound could be crystallized from acetonitrile (mp 172°–175° C. dec.). $^1$H NMR (CDCl$_3$): δ, 8.12, t, 1H, β or β'-CH=; 8.00, t, 1H, β or β'-CH=; 7.44–7.05, m, 18H, aromatic; 6.82, d, 2H, aromatic; 6.41, t, 1H, λ-CH=; 6.32, br d, 1H, α or α'-CH=; 6.18, d, 1H, α or α'-CH=; 4.36, t, 2H, 3" or 3'"-CH$_2$; 4.18, t, 2H, 3" or 3'"-CH$_2$; 3.86, q, 2H, 1'"-CH$_2$OH; 3.80, s, 3H, OCH$_3$; 3.43, br, 1H, OH; 3.11, t, 2H, 1"-CH$_2$OMMTr; 2.11, br m, 4H, 2", 2'"-CH$_2$; 1.70, s, 6H, CH$_3$; 1.68, s, 6H, CH$_3$. UV/visible spectrum (dichloromethane): λ$_{max}$ 644 nm (600 sh.); 370, 324, 244 nm.

1-(3"-(1"-(β-Cyanoethyl-N, N-diisopropylphosphoramidite)-propyl))-1'-(3'"-(1'"-(p-methoxytrityl)oxypropyl))-3,3,3',3'-tetramethylindodicarbocyanine chloride (XIV)

Compound XIII (4.0 g, 0.0051 mol) was dried by co-evaporation with dry acetonitrile, followed by dissolution in 33 mL of dry acetonitrile. A few grains of tetrazole were added to the solution, followed by the phosphitylating agent, bis-(N,N-diisopropyl)-β-cyanoethyl phosphordiamidite,[19] (2.32 g, 0.0077 mol). The reaction was monitored by TLC until the starting material was consumed. The solvent was evaporated and the flask evacuated under high vacuum for two hours. The resulting solid was triturated with dry ether at least five times, until the color of the ether was no longer green. The solid was then dried under high vacuum overnight and stored under argon at −20° C. Yield of compound XIV: approximately 4.0 g, purity by HPLC (C3 column, 90% acetonitrile/0.1M triethylammonium acetate), approximately 95%, monitored at 644 nm. $^1$H NMR (CDCl$_3$): δ, 8.35, dt, 2H, β, β'-CH=; 7.47–7.05, m, 18H, aromatic; 6.82, d, 2H, aromatic; 6.40, t, 1H, λ-CH=; 6.25, 6.18, dd, 1H, α, α'-CH=; 4.24, br m, 4H, 3", 3'"-CH$_2$; 3.95–3.55, m, 6H, 1'"-CH$_2$, isopropyl-CH, OCH$_2$CH$_2$CN; 3.78, s, 3H, OCH$_3$; 3.10, br t, 2H, CH$_2$OMMTr; 2.64, t, 2H, CH$_2$CN; 2.12, br m, 4H, 2", 2'"-CH$_2$; 1.82, 1.71, ds, 12H, CH$_3$; 1.22, dd, 12H, isopropyl CH$_3$. $^{31}$P NMR (CDCl$_3$+0.1% ethyldiisopropylamine, trimethyl phosphate standard) δ, 145.68 (purity~91%). UV/visible spectrum (dichloromethane): λ$_{max}$ 644 nm (600 sh.); 324, 282, 244 nm.

Example 2
(XIX, r=1, n=m=1, R=MMTr, R'=N,N-diisopropyl-O-β-cyanoethyl phosphoramidite, R"=R'"=R$^4$=R$^5$=H)

1-(3"-(1"-(β-Cyanoethyl-N,N-diisopropylphosphoramidite)-propyl))-1'-(3'"-(1'"-(p-methoxytrityl)oxypropyl))-3,3,3',3'-tetramethyl-indocarbocyanine chloride 1,1'-Bis-(3"-(1"-hydroxypropyl))-3,3,3',3'-tetramethyl-indocarbocyanine chloride (XIX, r=1, n=m=1, R=R'=R"=R'"=R$^4$=R$^5$=H)

1-(1'-Acetoxypropyl)-2,3,3-trimethyl-(3H)-indolinium iodide (5 g, 0.013 mol) was dissolved in 60 mL of pyridine and triethylorthoformate (0.038 mol, Aldrich) was added. The reaction mixture was refluxed for 1.5 hr, cooled, and evaporated. The residue was dissolved in 73 mL of 4M HCl mixed with 73 mL of methanol. The reaction was stirred overnight at ambient temperature. Some crystals which had formed were filtered and the filtrate evaporated to dryness. The residue was purified on a silica gel column with 5:5:5:85 methanol/ethyl acetate/acetone/dichloromethane, followed by 8:8:8:76 of the same. The pure fractions and the crystals were combined. HPLC: C18 column, 80% acetonitrile/0.1M triethylammonium acetate); UV/visible spectrum (80% acetonitrile/0.1M triethylammonium acetate, pH 7): λ$_{max}$ 545 nm (513 sh.); 280 nm. $^1$H NMR (CDCl$_3$): δ, 8.35, t, 1H, β-CH=; 7.38–7.14, m, 8H, aromatic; 6.84, d, 2H, α, α'-CH=; 4.75, t, 4H, 3, 3'-CH$_2$; 3.93, t, 2H, OH; 3.77, q, 4H, 1,1'-CH$_2$; 2.07, m, 4H, 2, 2'-CH$_2$; 1.68, s, 12H, CH$_3$.

1-(3'"-(1'"-Hydroxypropyl))-1'-(3"-(1"-(p-methoxytrityl)oxypropyl))-3,3,3',3'-tetramethyl-indocarbocyanine chloride (XIX, r=1, n=m=1, R=MMTr, R'=R"=R'"=R$^4$=R$^5$=H)

This compound was prepared in a procedure identical to that of compound XIII.

1-(3"-(1"-(β-Cyanoethyl-N,N-diisopropylphosphoramidite)-propyl))-1'-(3'"-(1'"-(p-methoxytrityl)oxypropyl))-3,3,3',3'-tetramethyl-indocarbocyanine chloride (XIX, r=1, n=m=1, R=MMTr, R'=N,N-diisopropyl-O-β-cyanoethyl phosphoramidite, R"=R'"=R$^4$=R$^5$=H)

This compound was prepared in a procedure identical to that of compound XIV. HPLC: C3 column, 90% acetonitrile/0.1M triethylammonium acetate; UV/visible spectrum (dichloromethane): λ$_{max}$ 556 nm (522 sh.); 282, 248, 232 nm. $^1$H NMR (CDCl$_3$): δ, 8.35, t, 1H, β-CH=; 7.45–7.00, m, 10H, aromatic+α, α'-CH=; 6.78, d, 2H, aromatic; 4.41, 4.30, 2 t, 4H, 3, 3'-CH$_2$; 3.96–3.40, m, 6H, 1"-CH$_2$, isopropyl-CH, OCH$_2$CH$_2$CN; 3.75, s, 3H, OCH$_3$; 3.10, br t, 2H, C H₂OMMTr; 2.64, t, 2H, CH₂CN; 2.29, 2.17, 2 m, 4H, 2", 2'''-CH₂; 1.70, 163, ds, 12H, CH₃; 1.22, d, 12H, isopropyl CH₃.

Example 3
(XIX, r=2, n=m=4, R=MMTr, R'=N,N-diisopropyl-O-β-cyanoethyl phosphoramidite, R"=R'''=R⁴=R⁵=H)

1-(6"-(1"-(β-Cyanoethyl-N,N-diisopropylphosphoramidite)-hexyl))-1'-(6'''-(1'''-(p-methoxytrityl)oxyhexyl))-3,3,3',3'-tetramethyl-indodicarbocyanine chloride In a method completely analogous to the preparation of Example 1, the compound named in Example 3 was prepared. The only difference was that 6-chlorohexyl acetate (Aldrich) was used instead of 3-chloropropyl acetate.

Example 4
(XIX, r=2, n=m=1, R=DMTr, R'=N,N-diisopropyl-O-β-cyanoethyl phosphoramidite, R"=R'''=R⁴=R⁵=H)

1-(3"-(1"-(β-Cyanoethyl-N,N-diisopropylphosphoramidite)-propyl))-1'-(3'''-(1'''-(p,p'-dimethoxytrityl)oxypropyl))-3,3,3', 3'-tetramethyl-indodicarbocyanine chloride In a method completely analogous to the preparation of Example 1, the compound named in Example 4 was prepared. The only difference was that dimethoxytrityl chloride (Chem Impex) was used instead of monomethoxytrityl chloride.

Example 5
(XIX, r=2, n=m=1, R=pivaloyl, R'=N,N-diisopropyl-O-β-cyanoethyl phosphoramidite, R"=R'''=R⁴=R⁵=H)

1-(3"-(1"-(β-Cyanoethyl-N,N-diisopropylphosphoramidite)-propyl))-1'-(3'''-(1'''-(pivaloyloxypropyl))-3,3,3',3'-tetramethyl-indodicarbocyanine chloride 1-(3'''-(1'''-Hydroxypropyl))-1'-(3"-( 1"-pivaloyloxypropyl))-3,3,3',3'-tetramethyl-indodicarbocyanine chloride Compound XII (1 g, 0.002 mol) was dissolved in 16 mL of dry pyridine and 0.182 mL (0.0015 mol) of pivaloyl chloride (Aldrich) was added. After five minutes the pyridine was evaporated and the residue was freed from residual pyridine by two co-evaporations each with toluene and dichloromethane. The product was purified by column chromatography on flash grade silica using 3:3:3:91 methanol/acetone/ethyl acetate/dichloromethane as the eluent. The appropriate fractions were carefully separated from the contaminating bis-pivaloyl compound. Yield: 0.15 g (10%). Purity=99+% by HPLC (90% acetonitrile/10% 0.1M TEAA mobile phase, C18 column 4.6×250 mm, flow rate: 1 mL/min, detector: 640 nm). UV/visible spectrum: $\lambda_{max}$ 640 (604, sh.) nm. ¹H NMR (CDCl₃): δ, 8.02, t, 1H, β or β'-CH=; 7.92, t, 1H, β or β'-CH=; 7.43–6.96, m, 8H, aromatic; 6.82, d, 2H, aromatic; 6.95, t, 1H, γ-CH=; 6.64, br d, 1H, α or α'-CH=; 6.27, d, 1H, α or α'-CH=; 4.38, t, 2H, 3" or 3'''-CH₂; 4.20, t, 2H, 3" or 3'''-CH₂; 4.11, t, 2H, 1"-CH₂OPiv; 3.88, q, 2H, 1'''-CH₂OH; 3.42, t, 1H, OH; 2.15, br m, 4H, 2", 2'''-CH₂; 1.74, d, 12H, CH₃; 1.29, s, 9H, Pivaloyl CH₃.

1-(3"-(1"-β-Cyanoethyl-N,N-diisopropylphosphoramidite)-propyl))-1'-(3'''-1'''-(pivaloyloxypropyl)-3,3,3',3'-tetramethyl-indodicarbocyanine chloride.

The pivaloyl derivative of XII (95 mg, 0.00016 mol) was dissolved in 0.8 mL of dry dichloromethane and one crystal of tetrazole was added. The phosphitylaing agent, bis-(N,N-diisopropyl)-β cyanoethyl phosphordimidite (96.8 mg, 0.00032 mol) was added and the reaction proceeded for 15 minutes. TLC analysis showed the conversion to the amidite to be almost quantitative. The reaction was evaporated to dryness and the residual solvent removed by evacuation under high vacuum. Excess phosphitylating reagent was removed by extraction with dry ether. The product was used without further purification to prepare a labelled oligonucleotide.

Example 6
Synthesis of an indodicarbocyanine labelled oligonucleotide.

Compound XIV (100 mg) was dissolved in 1 mL of dry acetonitrile (0.1M solution) and placed on an automated DNA synthesizer (Gene Assembler Plus®, Pharmacia LKB Biotechnology). After the synthesis of the 17 mer oligonucleotide using PAC protected nucleoside phosphoramidites (Pharmacia LKB Biotechnology), following the procedure suggested by the manufacturer, 50 μL of the solution of XIV was delivered to the reaction column with 100 μL of a 0.5M tetrazole activator solution. The mixture was cycled over the support containing the 5'-OH oligonucleotide for two minutes. Following the removal of excess XIV, the typical coupling cycle was completed by oxidiation, capping, and detritylation.[16]

The indodicarbocyanine-labelled oligonucleotide was deprotected in concentrated ammonia for 20 minutes at 60° C. The ammonia solution was desalted by gel filtration (NAP-10, Pharmacia LKB Biotechnology) and the product isolated by reverse phase HPLC: gradient of 10–40% A in B over 30 minutes; A=acetonitrile, B=0.1M triethylammonium acetate, pH 7. Retention time~15–20 minutes, depending on the length of the oligonucleotide. Gel electrophoresis: On an 18% polyacrylamide gel, the labelled oligonucleotide ran as a sharp band approximately 3 or 4 bases longer than the unlabelled oligo. The blue color of the dye was visible in the gel. UV/visible spectrum: $\lambda_{max}$ 648 (604, sh.) nm; 260 nm; $A_{260}/A_{648}=0.823$.

Example 7
Synthesis of a bis-indodicarbocyanine-labelled oligonucleotide

The compound named was synthesized as in Example 6, except that after the completion of the cycle adding the first indodicarbocyanine (including detritylation), a second indodicarbocyanine moiety was added. Deprotection and isolation were done in a manner analogous to that in Example 6. HPLC UV/visible spectrum: $\lambda_{max}$ 648 (604, sh.) nm; 260 nm

Example 8
Synthesis of a phosphoryl-indodicarbocyanine-labelled oligonucleotide The compound named was synthesized as in Example 6, except that after the completion of the cycle adding the first indodicarbocyanine (including detritylation), an amidite which yields a phosphate group on deprotection was added. Deprotection and isolation were both done in a manner analogous to that in Example 6. HPLC: C18 column, 10%–40% acetonitrile/0.1M triethylammonium acetate over 30 minutes; UV/visible spectrum: $\lambda_{max}$ 648 (604, sh.) nm; 260 nm

Example 9
(FIG. 7, XIX, r=2, n=m=1, R=MMTr, R'=N,N-diisopropyl-O-β-cyanoethyl phosphoramidite, R"=R'''=H, R⁴=R⁵=5,6-butadienyl)

Figure 9:
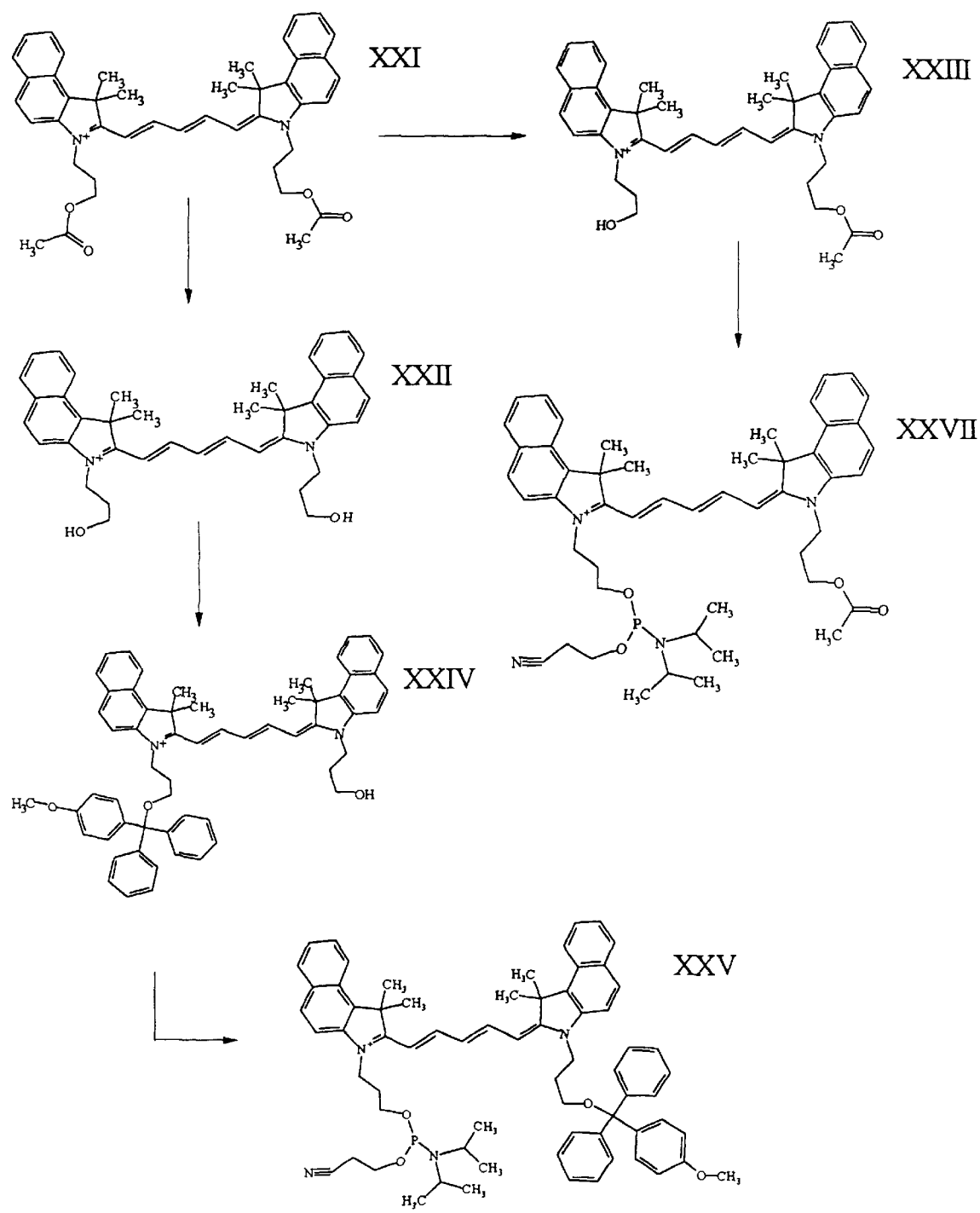
FIG. 9 shows the synthesis of Compound XXV.

1-(3"-(1"-(β-Cyanoethyl-N,N-diisopropylphosphoramidite)-propyl))-1'-(3"'-(1"'-(p-methoxytrityl)oxypropyl))-3,3,3',3'-tetramethyl-5.6-benzindodicarbocyanine chloride (XXV) FIG. 9

Figure 8:
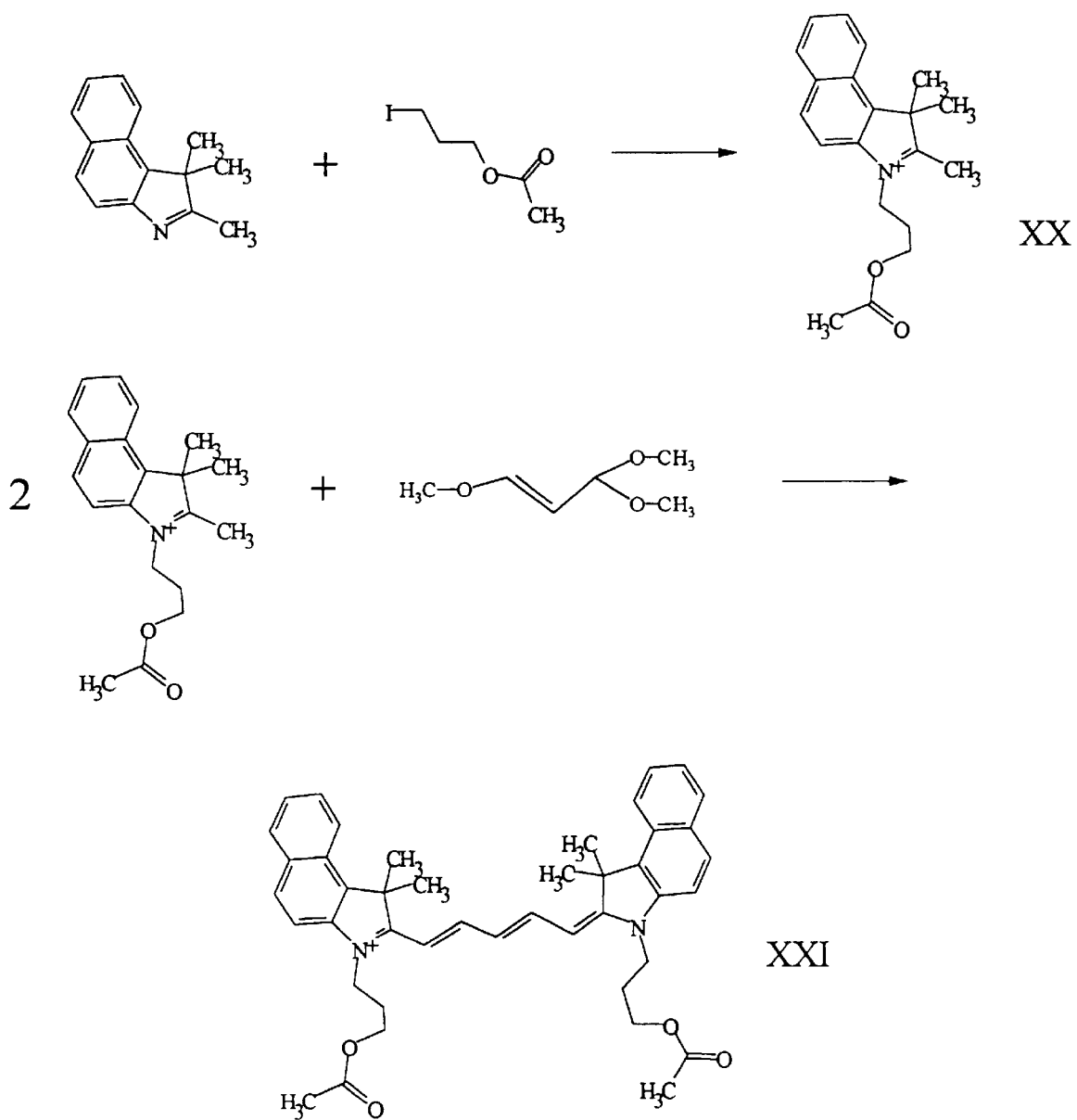
FIG. 8 shows the synthesis of Compound XXI.

1-((3'-(1'-Acetoxypropyl))-2,3,3-trimethyl-(3H)-benzindolinium iodide (XX) FIG. 8

3-Iodo-1-propyl acetate (6.84 g, 0.03 mol) and 2,3,3-trimethyl-(3H)-benzindole (6.27 g, 0.03 mol) were heated in a round bottom flask in an oil bath to 100° C. for three hours, then cooled to room temperature. The blue syrup solidified and was broken up and triturated with ethyl acetate. The solid was collected, washed with ether, and dried in vacuo. Yield: 8.8 g, 67% of 1-(1'-acetoxypropyl)-2,3,3-trimethyl-(3H)-benzindolinium iodide, (XX). TLC (silica) in 7% methanol, 10% ethyl acetate, 83% dichloromethane showed a single colorless main spot, visible by UV shadowing at $R_f$=0.3. UV spectrum, $\lambda_{max}$=220 nm; also 264, 304, 316, 380 nm.

1,1'-Bis-(3"-(1"-hydroxypropyl))-3,3,3',3'-tetramethyl-5.6-benzindodicarbocyanine chloride (XXII) FIG. 9

1-(1'-Acetoxypropyl)-2,3,3-trimethyl-(3H)-benzindolinium iodide, (XX), (4.37 g, 0.01 mol) was suspended in 30 mL dry acetonitrile with 0.85 mL of triethylamine and 0.28 mL of acetic acid in a round bottom flask. 1,3,3-Trimethoxypropene (1.01 mL, 0.005 mol, Kodak) was added and the mixture was refluxed for four hours in an oil bath heated to 100° C. TLC (silica) in 7% methanol, 10% ethyl acetate, 83% dichloromethane showed a single main spot of intense blue at $R_f$=0.25 and several minor spots. UV/visible spectrum, $\lambda_{max}$=680 nm; also 632 (sh), 362, 316, 302, 266, 256, 222 nm. (1,1'-bis-(3"-(1"-acetoxypropyl))-3,3,3', 3'-tetramethyl-5.6-benzindodicarbocyanine iodide) (XXI). FIG. 8

The solvent was evaporated, the mixture dissolved in 56 mL of methanol and added to 60 mL of 6M HCl to hydrolyze the acetyl groups. It was stirred overnight at room temperature. Because of the insolubility of the material in the methanol/HCl mixture, the process was repeated twice more. Finally, the material was crystallized from aqueous HCl. TLC showed the material to be a mixture of many compounds, including some starting diacetyl. The mixture was separated on a 200 cc column of silica gel using a step gradient of 0–5% methanol in 10% ethyl acetate/dichloromethane. A small amount of (1,1'-bis-(3"-(1"-acetoxypropyl))-3,3,3', 3'-tetramethyl-5.6-benzindodicarbocyanine chloride) (XXI) was recovered pure, the structure of which was confirmed by $^1$H NMR.

1-(3-(1'-acetoxypropyl))-1'-(3'-(1"-hydroxypropyl))-3,3,3',3'-tetramethyl-5.6-benzindodicarbocyanine chloride) (XXIII), the partially hydrolyzed material, was recovered in 1.2% yield (100 mg), the structure of which was confirmed by $^1$H NMR. 1,1'-Bis-(3"-(1"-hydroxypropyl))-3,3,3', 3'-tetramethyl-5.6-benzindodicarbocyanine chloride (XXII), was recovered in 8% yield (500 mg), the structure of which was confirmed by $^1$H NMR. The UV/visible spectra of XXI, XXII, and XXIII were nearly identical.

1-(3"'-(1"'-Hydroxypropyl))-1'-(3"-(1"-(p-methoxytrityl)oxypropyl))-3,3,3', 3'-tetramethyl-5.6-benzindodicarbocyanine chloride (XXIV) FIG. 9

Compound XXII (0.25 g, 0.000413 mol) was dried by co-evaporation with dry pyridine. It was dissolved in 2.5 mL of dry pyridine and 0.14 g (0.00043 mol) of monomethoxytrityl chloride (Aldrich) was added. The reaction was stirred for 30 minutes, at which point TLC (silica, 35% hexanes, 15% methanol, 50% dichloromethane) indicated the mixture contained the optimal amount of mono-trityl derivative possible. The reaction was quenched by the addition of methanol and the mixture evaporated to dryness. The residue was purified on a silica gel column with a step gradient of 40% hexanes, 2% methanol, 58% dichloromethane to 40% hexanes, 10% methanol, 50% dichloromethane as the eluent. Yield of compound XXIV was 0.18 g of 84% purity, the rest being the bis-trityl compound.

1-(3"-(1"-(β-Cyanoethyl-N,N-diisopropylphosphoramidite)-propyl))-1'-(3"'-(1"'-(p-methoxytrityl)oxypropyl))-3,3,3',3'-tetramethyl-5.6-benzindodicarbocyanine chloride (XXV) FIG. 9

Compound XXIV (0.18 g, 0.0021 mol) was dried by co-evaporation with dry acetonitrile, followed by dissolution in 2 mL of dry dichloromethane. A few grains of tetrazole were added to the solution, followed by the phosphitylating agent, bis-(N,N-diisopropyl)-β-cyanoethyl phosphordiamidite (0.095 g, 0.000315 mol). The reaction proceeded for 35 minutes at room temperature, at which time HPLC analysis showed it to be complete. The solvent was evaporated and the flask evacuated under high vacuum for one hour. The resulting solid was triturated with 10 mL dry ether three times. It was then dissolved in dichloromethane and extracted twice with 5% aqueous sodium bicarbonate. After drying and evaporation, the material was redissolved in dry acetonitrile, evaporated, and pumped dry at high vacuum. Yield of compound XXV was 0.2 g, and purity by HPLC (C3 column, 90% acetonitrile/0.1M triethylammonium acetate), monitored at 650 nm, 97.7%. UV/visible spectrum: $\lambda_{max}$ 682 (640, sh.), 360, 222 nm.

Figure 10:
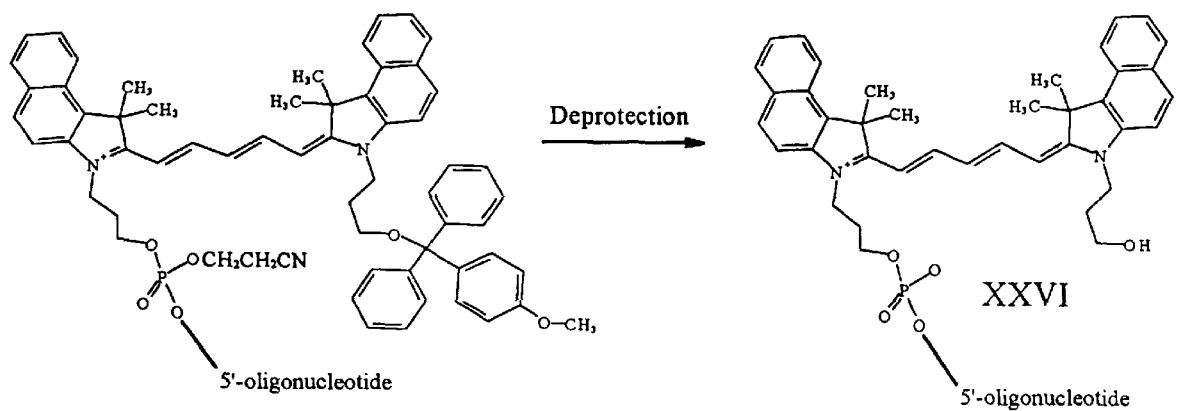
FIG. 10 shows the synthesis of Compound XXVI.
Figure 10:
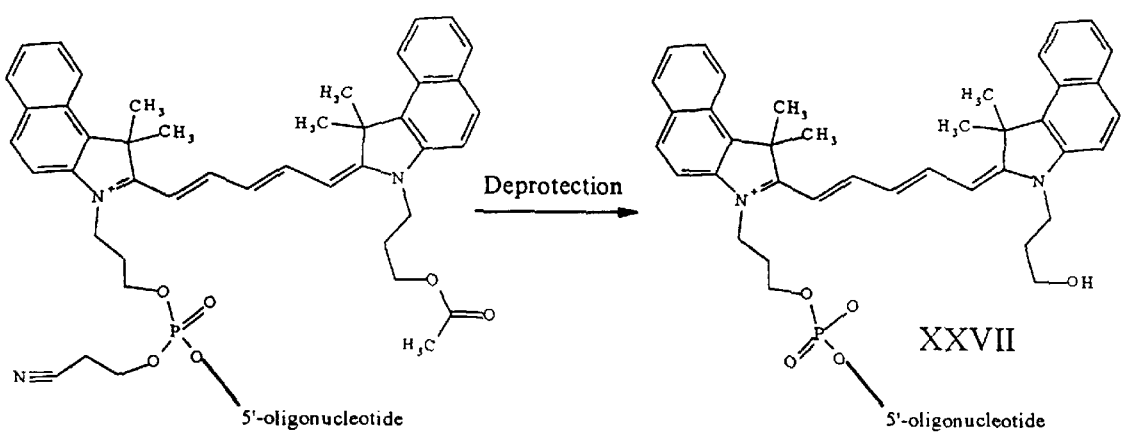

Example 10
Synthesis of a 5,6-benzindodicarbocyanine labeled oligonucleotide (XXVI) FIG. 10

Compound XXV (100 mg) was used to synthesize a labeled oligonucleotide on an automated DNA synthesizer (Gene Assembler Special™, Pharmacia LKB Biotechnology). After the synthesis of the 17 mer oligonucleotide using PAC protected nucleoside phosphoramidites (Pharmacia Biotech), following the procedure suggested by the manufacturer, 50 μL of the solution of XXV was delivered to the reaction column with 100 μL of a 0.5M tetrazole activator solution. The mixture was cycled over the support containing the 5'-OH oligonucleotide for two minutes. Following the removal of excess XXV, the typical coupling cycle was completed by oxidation, capping and detritylation.

The carbocyanine-labeled oligonucleotide was deprotected in concentrated ammonia for 30 minutes at 60° C. The ammonia solution was evaporated to dryness and the XXVI was isolated by reverse phase HPLC: gradient of 10–40% A in B over 30 minutes; A=acetonitrile, B=0.1M triethylammonium acetate, pH 7. Retention time ~19 minutes. UV/visible spectrum: $\lambda_{max}$ 682 (640, sh.) nm; 260 nm; $A_{260}/A_{648}$~0.8.

Example 11
1-(3"-(1"-(β-Cyanoethyl-N,N-diisopropylphosphoramidite)-propyl))-1'-(3"'-(1"'-(acetoxypropyl))-3,3,3',3'-tetramethyl-5.6-benzindodicarbocyanine chloride (XXVII) FIG. 9
(FIG. 7, XIX, r=2, n=m=1, R=acetyl, R'=N,N-diisopropyl-O-β-cyanoethyl phosphoramidite, R"=R"'=H, $R^4$=$R^5$=5, 6-butadienyl)

Compound XXIII (20 mg, 31 μmol) was co-evaporated three times with 0.2 mL of dry acetonitrile. It was redissolved in 0.2 mL of dry acetonitrile and a few crystals of tetrazole were added. The phosphitylating agent, bis-(N,N-diisopropyl)-β-cyanoethyl phosphordiamidite (15 mg, 50 μmol) was added and the reaction proceeded for 20 minutes. TLC analysis showed the conversion to the amidite to be almost quantitative. The reaction was evaporated to dryness and the residual solvent removed by evacuation under high vacuum. Excess phosphitylating reagent was removed by trituration with dry ether. $^1$H NMR and UV/visible spectroscopy showed the expected spectra for compound XXVII.

Example 12
Preparation of a 5.6-benzindodicarbocyanine-labeled oligonucleotide (XXVIII) FIG. 10

Compound XXVII was used without further purification to prepare a labeled oligonucleotide. A 24 mer oligonucleotide was synthesized using PAC amidites and the final 5' nucleotide was detritylated on the automated synthesizer. The solid support bearing the oligonucleotide was removed from the cassette and dried in a Sarstedt tube by co-evaporation with acetonitrile three times. Compound XXVII was dissolved in 100 μL dry acetonitrile and was added to the support, followed by 100 μL of 0.5M tetrazole in dry acetonitrile. The reaction proceeded for one hour; the supernatant was removed by centrifugation, and the support washed until no more blue color was present in the washing. The support was heated in concentrated ammonia at 60° C. for 20 minutes and the blue supernatant was passed through a NAP 10 column. The eluent was evaporated and the residue analyzed by HPLC.

Example 13
(FIG. 7, XIX, r=1, n=m=1, R=MMTr, R'=N,N-diisopropyl-O-β-cyanoethyl phosphoramidite, R"=R'"=H, R$^4$=R$^5$=5,6-butadienyl)

Figure 11:
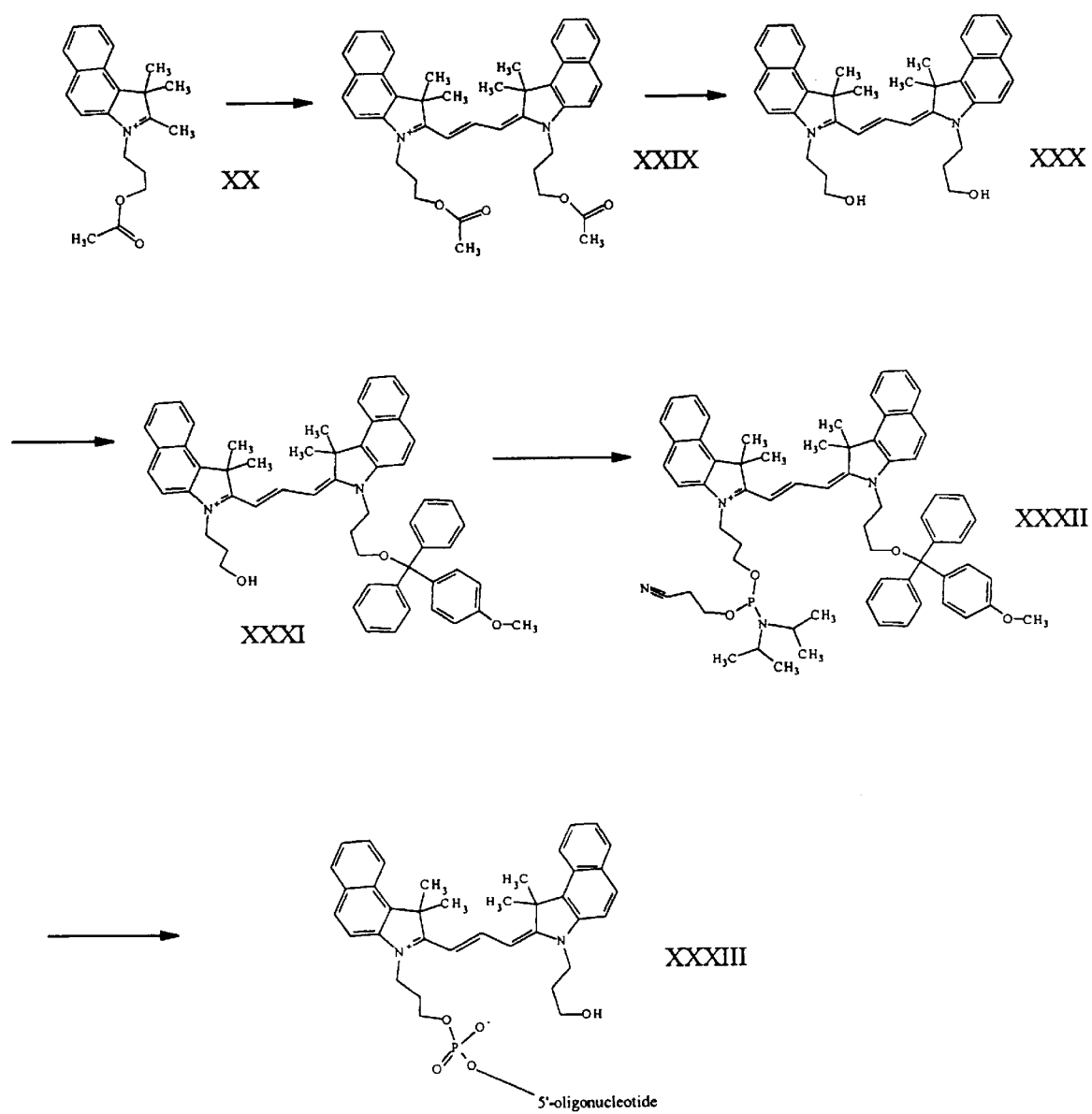
FIG. 11 shows the synthesis of Compound XXXIII.

1-(3"-(1"-(β-Cyanoethyl-N,N-diisopropylphosphoramidite)-propyl))-1'-(3'"-(1'"-(p-methoxytrityl)oxypropyl))-3,3,3',3'-tetramethyl-5.6-benzindocarbocyanine chloride (XXXII) FIG. 11

1,1'-Bis-(3"-(1"-hydroxypropyl))-3,3,3',3'-tetramethyl-5.6-benzindocarbocyanine chloride (XXX) FIG. 11

1-(1'-Acetoxypropyl)-2,3,3-trimethyl-(3H)-benzindolinium iodide, (XX), (2 g, 0.0046 mol) was dissolved in 22 mL of pyridine and 2 mL triethylorthoformate (Aldrich) was added. The reaction mixture was refluxed for 2 hours, cooled, and evaporated to a solid. HPLC analysis indicated the product, 1,1'-bis-(3"-(1"-acetoxypropyl))-3,3,3',3'-tetramethyl-5.6-benzindocarbocyanine (XXIX), was 98% pure. UV/vis λ$_{max}$ 583 nm. The solid was dissolved in 25 mL of methanol and mixed with 25 mL of 6M HCl. The reaction was stirred overnight at ambient temperature. The filtrate was evaporated to half volume, cooled, and the crystals of XXX collected. 98% purity by HPLC: C18 column, 80% acetonitrile/0.1M triethylammonium acetate); UV/visible spectrum (80% acetonitrile/01.M triethylammonium acetate, pH 7): λ$_{max}$ 583 nm (550 sh.); 335 nm. Yield: 1.25 g, 46%.

1-(3'"-(1'"-Hydroxypropyl))-1'-(3"-(1"-(p-methoxytrityl)oxypropyl))-3,3,3',3'-tetramethyl-5.6-benzindocarbocyanine chloride (XXXI) FIG. 11

Compound XXX, (1.25 g, 0.0021 mol) in 10 mL dry pyridine was treated with 0.6 g (0.0021 mol) of monomethoxytrityl chloride for 45 minutes. The reaction was quenched with methanol and evaporated to a gum. The product XXXI was purified on a 60 mL flash silica column with a step gradient of hexane/dichloromethane/methanol, 40:60:0 to 40:54:6. The fractions were monitored by HPLC (C3 column, 90% acetonitrile, isocratic). The pooled fractions were evaporated. Purity by HPLC (as above): 98%. UV/vis: 587 (553 sh); 330 nm. Yield: 0.7 g, 39%.

1-(3"-(1"-(β-Cyanoethyl-N,N-diisopropylphosphoramidite)-propyl))-1'-(3'"-(1'"-(p-methoxytrityl)oxypropyl))-3,3,3',3'-tetramethyl-5.6-benzindocarbocyanine chloride (XXXII) FIG. 11

Compound XXXI (0.7 g, 0.00082 mol) was dissolved in 7 mL of dry dichloromethane; a few grains of tetrazole were added followed by 0.37 g (0.00123 mol) of bis-(N,N-diisopropyl)-β-cyanoethyl phosphordiamidite. After 2 hours, 50 mg more bis-(N,N-diisopropyl)-β-cyanoethyl phosphordiamidite and a few more grains of tetrazole were added. The solution was evaporated to dryness, the solid triturated with ether twice, dissolved in dichloromethane, extracted with aqueous bicarbonate, dried, and evaporated. Purity by HPLC: (C3 column, 90% acetonitrile/0.1M triethylammonium acetate), 94%; UV/visible spectrum (90% acetonitrile/0.1M triethylammonium acetate): λ$_{max}$ 579 nm (550 sh.); 325 nm.

Example 14
Preparation of a 5.6-benzindocarbocyanine-labeled oligonucleotide (XXXIII) FIG. 11

Compound XXXII was used without further purification to prepare a labeled oligonucleotide. A 24 mer oligonucleotide corresponding to the M13 −40 sequencing primer was synthesized using PAC amidites and the final 5' nucleotide was detritylated on the automated synthesizer. The solid support bearing the oligonucleotide was removed from the cassette and dried in a Sarstedt tube by co-evaporation with acetonitrile three times. Compound XXXII was dissolved in 100 μL dry acetonitrile and was added to the support, followed by 100 μL of 0.5M tetrazole in dry acetonitrile. The reaction proceeded for one hour; the supernatant was removed by centrifugation, and the support washed until no more blue color was present in the washing.

The support was heated in concentrated ammonia at 60° C. for 30 minutes, the pink supernatant evaporated, and the residue analyzed by HPLC (C18, 10–80% acetonitrile in 0.1M TEAA). The major peak had the expected UV/visible spectrum and $A_{260}/A_{583}$ ratio for the 5,6-benzindocarbocyanine-labeled 24 mer, XXXIII: 583 (553 sh); 326, 258; $A_{260}/A_{583}$=2.12.

In the following structure

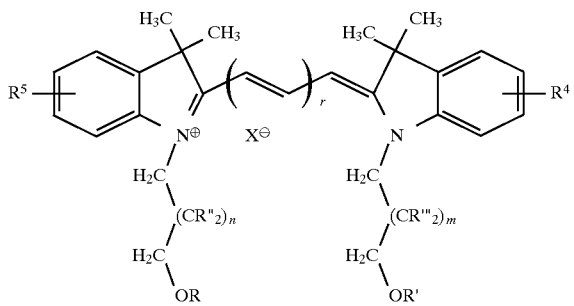

$R^4$ and $R^5$ are selected from 5,6; 6,7; or 7,8-

(butadienyl). This is meant to indicate that the indolenine phenyl ring may be fused to a second phenyl ring at any of the positions shown below:

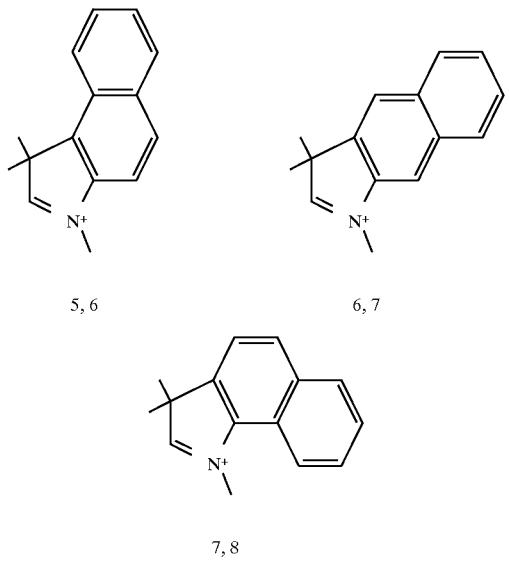

Although the present invention has been described in considerable detail with reference to certain preferred versions thereof, other versions are possible. For example, where $R_4$ and $R_5$ are $CH_2COOR$ and where R is an alkyl or COOR or $CH_2OP=O$ (O-cyanoethyl)$_2$.

Therefore, the spirit and scope of the appended claims should not be limited to the description of the preferred versions contained herein.

1. Brumbaugh, J. A.; Middendorf, L. R.; Grone, D. L.; Ruth, J. R., *Proc. Nat. Acad. Sci. U.S.A.* 1988, 85, 5610–5614.
2. Kaiser, R. J.; MacKellar, S. L.; Vinayak, R. S.; Sanders, J. Z.; Saavedra, R. A.; Hood, L. E.; *Nuc. Acids Res.* 1989, 17, 6087–6102.
3. Coull, J. M.; Weith, H. L.; Bischoff, R.; *Tetrahedron Lett.* 1986, 27, 3991–3994.
4. Ansorge, W.; Sproat, B. S.; Stegemann, J.; Schwager, C., *J. Biochem. Biophys. Methods* 1986, 13, 315–323.
5. (a) Pochet, S.; Huynh-Dinh, T.; Igolen, J. *Tetrahedron* 1988, 43, 3481. (b) Haralambidis, J.; et al., *Tetrahedron Lett.* 1987, 28, 5199. (c) Urdea, M. S.; Warner, B. D., Running, J. A.; Stempien, M.; Clyne, J.; Horn, T. *Nuc. Acids Res.* 1988, 16, 4937. (d) Le Brun, S.; Duchange, N.; Namane, A.; Zakin, M. M.; Huynh-Dinh, T.; Igolen, J. *Biochemie* 1989, 71, 319.
6. Bannwarth, W.; Schmidt, D. *Tetrahedron Lett.* 1989, 30, 1513–1516.
7. Alves, A. M.; Holland, D.; Edge, M. D. *Tetrahedron Lett.* 1989, 30, 3089–3092.
8. Roget, A.; Bazin, H.; Teoule, R. *Nuc. Acids Res.* 1989, 17, 7643–7651.
9. Trainor, G. L.; Cocuzza, A. J.; Hobbs, F. W.; Johnson, P. R.; Emmett, G. E.; Zagursky, R. J.; Livak, K. J.; Korolkoff, P. N.; Jensen, M. A. (Poster at Cold Spring Harbor Conference, April, 1989, entitled "Chemical Reagents for Molecular Biology").
10. Schubert, F.; Ahlert, K.; Cech, D.; Rosenthal, A. *Nuc. Acids Res.* 1990, 18, 3427.
11. For a general reference, see *The Cyanine Dyes and Related Compounds*, Frances M. Hamer, Interscience, New York, 1964, Ch. 7.
12. Yu. H.; Ernst, L.; Wagner, M.; Waggoner, A. *Nuc. Acids Res.* 1992, 20, 83–88.
13. (a) U.S. Pat. No. 4,981,977, Southwick, P. L.; Waggoner, A. S. (b) Southwick, P. L.; Ernst, L. A.; Tauriello, E. W.; Parker, S. R.; Mujumdar, R. B.; Mujumdar, S. R.; Clever, H. A.; Waggoner, A. S. *Cytometry*, 1990, 11, 418–430. (c) Patonay, G.; Antoine, M. D., *Anal. Chem.*, 1991, 63, 321–326A. (d) Galbraith, W.; Wagner, M. C. E.; Chao, J.; Abaza, M.; Ernst, L. A.; Nederlof, M. A.; Hartsock, R. J.; Taylor, D. L.; Waggoner, A. S., *Cytometry*, 1991, 12, 579–596.
14. Wessendorf, M. W.; Brelje, T. C., *Histochemistry*, 1992, 98, 81–85.
15. Ernst, L. A.; Gupta, R. K.; Mujumdar, R. B.; Waggoner, A. S., *Cytometry*, 1989, 10, 3–10.
16. Pharmacia LKB Biotechnology Gene Assembler Plus® Manual.
17. Schulhof, J. C.; Molko, D.; Teoule, R., *Nuc. Acids Res.*, 1987, 15, 397–316. (Available from Pharmacia LKB Biotechnology and several others.)
18. Agrawal, S.; Zamecnik, P. C., *Nuc. Acids Res.*, 1990, 18, 5419–5423.
19. Gaffney, B.; Jones, R. A., *Biochemistry*, 1989, 28, 5882.

We claim:

1. A chemical compound of the following formula:

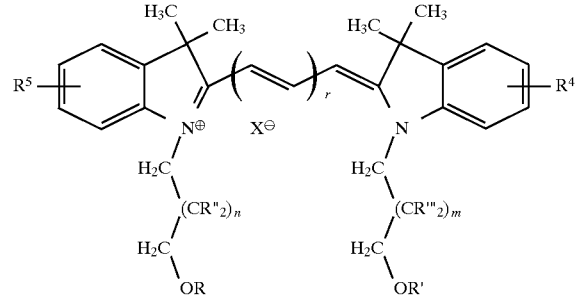

wherein:

R is selected from the group consisting of H, trityl, 4-O-monomethoxytrityl, 4,4'-O-dimethoxytrityl, and acyl groups,

and whereby R can be used as a protecting group or is an H;

R' is a phosphoramidite;

R" is selected from the group consisting of H and lower alkyl groups;

R''' is selected from the group consisting of H and lower alkyl groups;

$R^4$ is selected from the group consisting of H, lower alkyl, acyl,

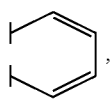

and $(CH_2)_pCOO(CH_2)_qCH_3$ wherein p is an integer from 0 to 4 and q is an integer from 0 to 4;

$R^5$ is selected from the group consisting of H, lower alkyl, acyl,

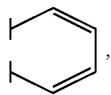

and $(CH_2)_pCOO(CH_2)_qCH_3$ wherein p is an integer from 0 to 4 and q is an integer from 0 to 4;

n is an integer from 0 to 10;
m is an integer from 0 to 10;
r is 1, 2, or 3; and
$X^-$ is a negative ion.

2. The chemical compound of claim 1 wherein:
R is 4-O-monomethoxytrityl;
R' is N,N-diisopropyl-O-β-cyanoethyl phosphoramidite;
R" and R''' are H;
n is 1;
m is 1;
r is 2; and
$R^4$ and $R^5$ are 5,6-butadienyl.

3. The chemical compound of claim 1 wherein:
R is 4-O-monomethoxytrityl;
R' is N,N-diisopropyl-O-β-cyanoethyl phosphoramidite;
R" and R''' are H;
n is 1;
m is 1;
r is 1; and
$R^4$ and $R^5$ are 5,6-butadienyl.

4. The chemical compound of claim 1 wherein:
R is acetyl;
R' is N,N-diisopropyl-O-β-cyanoethyl phosphoramidite;
R" and R''' are H;
n is 1;
m is 1;
r is 2; and
$R^4$ and $R^5$ are 5,6-butadienyl.

5. A chemical compound of the following formula:

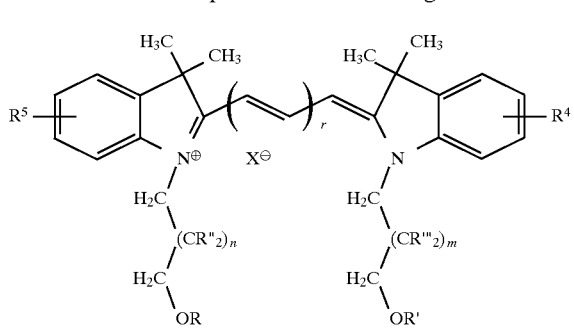

wherein:

R is selected from the group consisting of aryl-group-containing moieties, wherein the moiety does not interfere with the attachment of an oligonucleotide at the R' position;
R' is a oligonucleotide;
R" is selected from the group consisting of H and lower alkyl groups;
R''' is selected from the group consisting of H and lower alkyl groups;
$R^4$ is selected from the group consisting of H, lower alkyl, acyl,

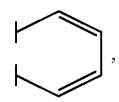

and $(CH_2)_pCOO(CH_2)_qCH_3$ wherein p is an integer from 0 to 4 and q is an integer from 0 to 4;

$R^5$ is selected from the group consisting of H, lower alkyl, acyl,

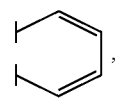

and $(CH_2)_pCOO(CH_2)_qCH_3$ wherein p is an integer from 0 to 4 and q is an integer from 0 to 4;

n is an integer from 0 to 10;
m is an integer from 0 to 10;
r is 1, 2, or 3; and
$X^-$ is a negative ion.

6. A benzindocarbocyanine dye attached to a phosphoramidite, said dye comprising a benzindolinium ring and a benzindolenine ring in resonance
  wherein said rings are connected by a carbon chain with conjugated double bonds,
  wherein the rings each have a dimethyl substituent at the 3 position,
  wherein said phosphoramidite is attached through a first linker at the nitrogen of either ring,
  wherein a protecting group is attached through a second linker at the nitrogen of the other ring, and
  wherein no glyceryl linker is interposed between (a) said protecting group and said phosphoramidite and (b) said benzindocarbocyanine dye.

7. A method of attaching a fluorescent label to an oligonucleotide, comprising:
  reacting the compound of claim 1 with the oligonucleotide such that the label becomes linked to the oligonucleotide.

8. The method of claim 7 wherein the reacting step comprises linking a 5' end of the oligonucleotide to a phosphorus on the compound, oxidizing the linkage product, and removing the protecting group R from the oxidized linkage product.

9. The method of claim 8 wherein the linkage is done in the presence of tetrazole and acetonitrile.

* * * * *